United States Patent

Böckmann et al.

[11] Patent Number: 4,650,809
[45] Date of Patent: Mar. 17, 1987

[54] CYCLIC AZOLYLVINYL ETHER FUNGICIDES

[75] Inventors: Klaus Böckmann, Cologne; Gerhard Jäger, Leverkusen; Wilhelm Brandes, Leichlingen; Paul Reinecke, Leverkusen, all of Fed. Rep. of Germany

[73] Assignee: Bayer Aktiengesellschaft, Leverkusen, Fed. Rep. of Germany

[21] Appl. No.: 727,720

[22] Filed: Apr. 26, 1985

[30] Foreign Application Priority Data

May 11, 1984 [DE] Fed. Rep. of Germany ....... 3417467

[51] Int. Cl.$^4$ .................. A01N 43/50; A01N 43/653; C07D 407/04
[52] U.S. Cl. ...................... 514/383; 514/184; 514/397; 548/101; 548/262; 548/336
[58] Field of Search ............ 548/101, 262, 336; 514/184, 383, 397

[56] References Cited

U.S. PATENT DOCUMENTS

| 4,291,044 | 9/1981 | Jäger et al. ................. 514/383 |
| 4,351,839 | 9/1982 | Chan ........................ 548/262 X |
| 4,421,758 | 12/1983 | Kawamoto et al. ............ 548/262 X |
| 4,582,843 | 4/1986 | Timmler et al. .............. 548/262 X |

FOREIGN PATENT DOCUMENTS

| 0008804 | 3/1980 | European Pat. Off. . |
| 0023756 | 2/1981 | European Pat. Off. . |
| 0028363 | 5/1981 | European Pat. Off. . |
| 0079856 | 5/1983 | European Pat. Off. . |
| 0123931 | 11/1984 | European Pat. Off. . |

| 2610022 | 9/1976 | Fed. Rep. of Germany . |
| 2638470 | 3/1977 | Fed. Rep. of Germany . |
| 2757113 | 6/1979 | Fed. Rep. of Germany . |
| 2839388 | 3/1980 | Fed. Rep. of Germany . |

OTHER PUBLICATIONS

Marchington et al., Chemical Abstracts, vol 100(1984) 103338d.

*Primary Examiner*—Richard L. Raymond
*Attorney, Agent, or Firm*—Sprung Horn Kramer & Woods

[57] ABSTRACT

Fungicidally active novel cyclic azolylvinyl ethers of the formula

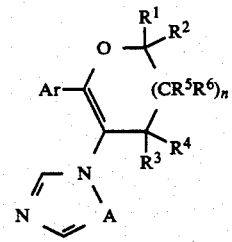

in which
A is a nitrogen atom or the CH group;
Ar is optionally substituted phenyl,
$R^1$ to $R^6$ each independently is hydrogen or alkyl, and
n is 0 to 1, or addition products thereof with acids or metal salts 8 Claims, No Drawings

CYCLIC AZOLYLVINYL ETHER FUNGICIDES

The present invention relates to new cyclic azolylvinyl ethers, a process for their preparation and their use as fungicides.

It is already known that certain 1-ethene-azolyl derivatives, such as, for example, 2-(4-chlorophenoxy)-4,4-dimethyl-1-(imidazol-1-yl)-1-penten-3-one, have good fungicidal properties (compare DE-OS No. (German Published Specification) 2,846,980).

It is also already known that certain arylvinylazolyl ethers have good fungicidal properties (compare DE-OS No. (German Published Specification) 2,757,113, DE-OS No. (German Published Specification) 2,839,388 and European Patent No. 0,079,856).

It is furthermore already known that disulphides, such as, for example, zinc ethylene-1,2-bisdithiocarbamidate, are good agents for combating fungal plant diseases (compare R. Wegler, "Chemie der Pflanzenschutz- und Schädlingsbekämpfungsmittel" ("Chemistry of plant protection agents and agents for combating pests"), volume 2, page 59 et seq., Springer Verlag 1970).

However, the action of these compounds is not always completely satisfactory in certain fields of indication, especially when low amounts and concentrations are applied.

New cyclic azolylvinyl ethers of the general formula (I)

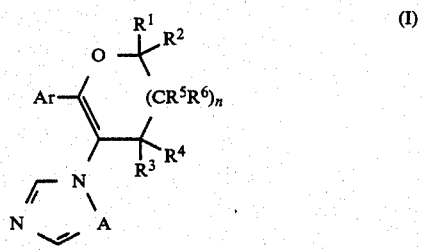

in which
  A represents a nitrogen atom or the CH group,
  Ar represents optionally substituted phenyl,
  $R^1$ to $R^6$ are identical or different and represent hydrogen or alkyl and
  n represents 0 or 1, and acid addition salts and metal salt complexes thereof, have been found.

It has furthermore been found that the new cyclic azolylvinyl ethers of the formula (I) are obtained by a process in which azolylvinyl ketones of the formula (II)

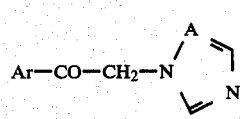

in which
  A and Ar have the abovementioned meaning, are reacted with compounds of the formula (III)

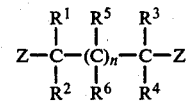

in which
  $R^1$ to $R^6$ and the index n have the abovementioned meaning and
  Z represents an electron-withdrawing leaving grouping, in the presence of a strong base and in the presence of an aprotic, polar diluent, or in an aqueous-organic two-phase system in the presence of a phase transfer catalyst.

If appropriate, an acid or a metal salt can then be added onto the compounds of the formula (I) thus obtained.

It has furthermore been found that the new cyclic azolylvinyl ethers of the formula (I) have powerful fungicidal properties. Surprisingly, the compounds according to the invention thereby exhibit better fungicidal actions than the compounds 2-(4-chlorophenoxy)-4,4-dimethyl-1-imidazol-1-yl)-1-penten-3-one and zinc ethylene-1,2-bisdithiocarbamidate, which are known from the prior art. The active compounds according to the invention thus represent an enrichment of the art.

Formula (I) provides a general definition of the cyclic azolylvinyl ethers according to the invention. In this formula, preferably,
  A represents a nitrogen atom or the CH group,
  Ar represents phenyl which is optionally monosubstituted or polysubstituted by identical or different substituents, substituents which may be mentioned being: halogen, alkyl and alkoxy with in each case 1 to 4 carbon atoms, halogenoalkyl, halogenoalkoxy and halogenoalkylthio with in each case 1 or 2 carbon atoms and 1 to 5 identical or different halogen atoms, nitro, cyano, in each case optionally halogen-substituted phenyl and phenoxy, and cycloalkyl with 5 or 6 carbon atoms;
  $R^1$ to $R^6$, which can be identical or different, represent hydrogen or straight-chain or branched alkyl with 1 to 4 carbon atoms, and the index n represents 0 or 1.

Particularly preferred compounds of the formula (I) are those
in which
  A represents a nitrogen atom or the CH group,
  Ar represents phenyl which is optionally mono-, di- or tri-substituted by identical or different substituents, substituents which may be mentioned being: fluorine, chlorine, bromine, methyl, ethyl, methoxy, trifluoromethyl, trifluoromethoxy, trifluoromethylthio, nitro and cyano, phenyl and phenoxy, in each case optionally substituted by chlorine or fluorine, and cyclohexyl,
  $R^1$ to $R^6$, which can be identical or different, represent hydrogen, methyl, ethyl or isopropyl; and
  the index n represents 0 or 1.

Preferred compounds according to the invention are also addition products of acids and those cyclic azolylvinyl ethers of the formula (I) in which the substituents A, Ar and $R^1$ to $R^6$ and the index n have the meanings which have already been given as preferred for these substituents and the index.

Preferred acids which can be added on include hydrogen halide acids, such as, for example, hydrochloric acid and hydrobromic acid, in particular hydrochloric acid, and furthermore phosphoric acid, nitric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as p-toluenesulphonic acid and 1,5-naphthalenedisulphonic acid.

Compounds according to the invention which are also preferred are addition products of salts of metals of main groups II to IV and sub-groups I and II and IV to VIII and those cyclic azolylvinyl ethers of the formula (I) in which the substituents A, Ar and $R^1$ to $R^6$ and the index n have the meaning which have already been mentioned as preferred for these substituents and the index.

Salts of copper, zinc, manganese, magnesium, tin, iron and nickel are particularly preferred here. Possible anions of these salts are those which are derived from acids which lead to physiologically acceptable addition products. In this connection, particularly preferred acids of this type are the hydrogen halide acids, such as, for example, hydrochloric acid and hydrobromic acid, and nitric acid and sulphuric acid.

If, for example, 4-biphenylyl 1,2,4-triazol-1-ylmethyl ketone and 1,3-dibromopropane in the presence of sodium hydride are used as starting substances, the course of the reaction in the process according to the invention can be represented by the following equation:

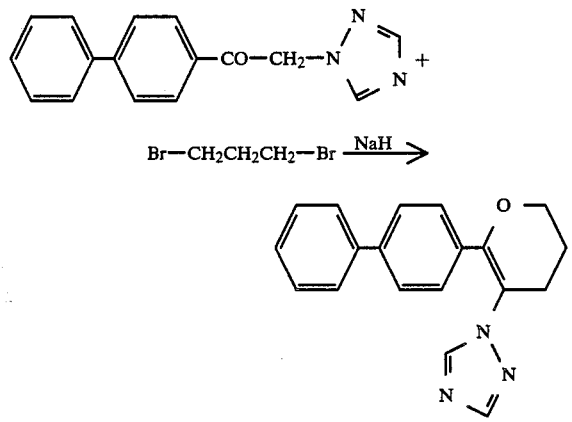

Formula (II) provides a general definition of the azolylmethyl ketones to be used as starting substances in carrying out the process according to the invention. In this formula, A and Ar preferably have those meanings which have already been mentioned as preferred for these substituents in connection with the description of the substances of the formula (I) according to the invention.

The azolylmethyl ketones of the formula (II) are known (in this context, compare, for example, DE-OS No. (German Published Specification) 2,431,407, DE-OS No. (German Published Specification) 2,610,022 and DE-OS No. (German Published Specification) 2,638,470) and they are obtained in a generally known manner, by reacting the corresponding halogenomethyl ketones with imidazole or 1,2,4-triazole in the presence of a diluent, such as, for example, acetonitrile, and in the presence of an acid-binding agent, such as, for example, triethylamine.

Formula (III) provides a general definition of the compounds also to be used as starting substances for the process according to the invention. In this formula, $R^1$ to $R^6$ and the index n preferably have those meanings which have already been mentioned as preferred for these substituents and the index in connection with the description of the substances of the formula (I) according to the invention. Z preferably represents an electron-withdrawing leaving grouping, such as, for example, halogen, p-methylphenylsulphonyloxy, the grouping $—O—SO_2—OR$ or $—NR_3$ and the like, R here representing, for example, alkyl with 1 to 4 carbon atoms.

The compounds of the formula (III) are generally known compounds of organic chemistry, or they can be obtained in a known manner.

Possible diluents for the process according to the invention are aprotic polar solvents. These include, preferably, dimethylformamide, dimethylacetamide, dimethylsulphoxide, N-methylpyrrolidine, 2-pyrrolidinone and hexamethylphosphoric acid triamide. In some cases, it may be advantageous to mix these solvents with other customary inert organic solvents, such as, for example, aromatic hydrocarbons.

The process according to the invention is carried out in the presence of a strong base. All the usual organic and, in particular, inorganic bases can be employed here, such as, preferably, alkali metal hydrides, hydroxides or carbonates, such as, for example, sodium hydride and sodium hydroxide, and tertiary amines, such as triethylamine, piperidine and pyridine.

The reaction temperatures can be varied within a substantial range in carrying out the process according to the invention. In general, the reaction is carried out between $-20°$ C. and $100°$ C., preferably between $20°$ C. and $100°$ C.

In carrying out the process according to the invention, 1 to 2 moles of compound of the formula (III) are preferably employed per mole of azolylmethyl ketone of the formula (II). The end products of the formula (I) are isolated in the generally customary manner. Any byproducts which may occur, which are formed by alkylation on the $CH_2$ group, are thereby separated off in the usual manner, such as, for example, by column chromatography or recrystallization.

The process according to the invention can also be carried out in a two-phase system, such as, for example, aqueous sodium hydroxide solution or potassium hydroxide solution/toluene or methylene chloride, if appropriate with the addition of 0.1 to 1 mole of a phase transfer catalyst, such as, for example, ammonium or phosphonium compounds, examples which may be mentioned being benzododecyl-dimethyl-ammonium chloride and triethyl-benzylammonium chloride.

The acid addition salts of the compounds of the formula (I) can be obtained in a simple manner by customary salt formation methods, for example by dissolving a compound of the formula (I) in a suitable inert solvent and adding the acid, for example hydrochloric acid, and, if appropriate, they can be purified by washing with an organic solvent.

The metal salt complexes of compounds of the formula (I) can be obtained in a simple manner by customary processes, thus, for example, by dissolving the metal salt in alcohol, for example ethanol, and adding the solution to compounds of the formula (I). The metal salt complexes can be purified in a known manner, for example by filtration.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Some causative organisms of fungal and bacterial diseases, which fall under the generic names listed above, may be mentioned as examples but not by way of limitation: Botrytis species, such as, for example, *Botrytis cinerea;* Plasmopara species, such as, for example, *Plasmopara viticola;* Uromyces species, such as, for example, *Uromyces appendiculatus;* Sphaerotheca species, such as, for example, *Sphaerotheca fuliginea;* Venturia species, such as, for example, *Venturia inaequalis;* Podosphaera species, such as, for example, *Podosphaera leucotricha;* Phytophthora species, such as, for example, *Phytophthora infestans;* Erysiphe species, such as, for example, *Erysiphe graminis;* Puccinia species, such as, for example, *Puccinia recondita;* Fusarium species, such as, for example, *Fusarium culmorum;* Ustilago species, such as, for example, *Ustilago nuda* or *Ustilago avenae;* Septoria species, such as, for example, *Septoria nodorum;* Tilletia species, such as, for example, *Tilletia caries;* Xanthomonas species, such as, for example *Xanthomonas oryzae;* Pseudomonas species, such as, for example, *Pseudomonas lachrymans;* Pyricularia species, such as, for example, *Pyricularia oryzae;* Pellicularia species, such as, for example, *Pellicularia sasakii,* Pyrenophora species, such as, for example, *Pyrenophora teres* (conidia form: Drechslera, syn. Helminthosporium), Cochliobolus species, such as, for example, *Cochliobolus sativus* (conidia form: Drechslera, syn. Helminthosporium) and Cercospora species, such as, for example, *Cercospora canescens.*

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Venturia species, such as against the apple scab causative organism (*Venturia inaequalis*); cereal diseases, such as *Cochliobolus sativus, Leptosphaeria nodorum, Erysiphe graminis* and *Pyrenophora teres-*, and rice diseases, such as *Pyricularia oryzae* and *Pellicularia sasakii.* The substances according to the invention also exhibit a broad, good in vitro fungicidal action spectrum.

When applied in appropriate amounts, the substances according to the invention also exhibit bactericidal and growth-regulating properties.

The active compounds can be converted to the customary formulations, such as solutions, emulsions, wettable powders, suspensions, powders, dusts, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strong polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylenefatty alcohol ethers, for example alkylaryl polyglycol ethers, alkyl sulphonates, alkylsulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs and azo- and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

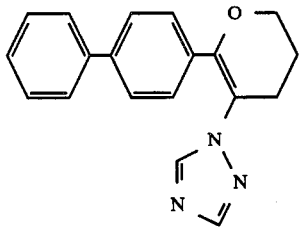

6 g of sodium hydride (80% strength) are added to a solution of 26.4 g of 1-(4-phenylphenacyl)-1,2,4-triazole and 20.2 g of 1,3-dibromopropane in 100 ml of dry dimethylformamide at room temperature in the course of 4 hours. The mixture is stirred at room temperature for 24 hours and at 30° C. for 5 hours and is then concentrated in vacuo. The residue is taken up in 300 ml of ethyl acetate/toluene (1:1) and 200 ml of water. The organic phase is separated off, washed twice with water, dried over sodium sulphate and concentrated in vacuo. 20 ml of ethanol are added to the residue, and water is added until the mixture becomes cloudy. After a few hours, the crystalline precipitate is filtered off with suction and recrystallized from 90% strength ethanol.

12.2 g (40.3% of theory) of 1-(4-biphenyl-yl)-2-(1,2,4-triazol-1-yl)-4,5-dihydropyran of melting point 113° C. are obtained.

The following compounds of the formula (I) can be obtained in a corresponding manner, in accordance with the process conditions described:

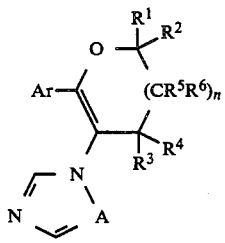

| Example No. | A | Ar | $-CR^1R^2(-CR^5R^6)_{\overline{n}}CR^3R^4-$ | Melting point (°C.) |
|---|---|---|---|---|
| 2 | N | 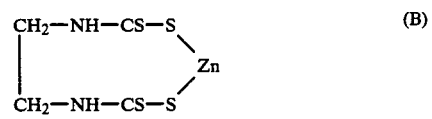 | $-CH_2-CH_2-CH_2-$ | 87–88 |
| 3 | CH | | $-CH_2-CH_2-CH_2-$ | 151 |

Use examples

The compounds shown below are used as comparison substances in the examples which follow:

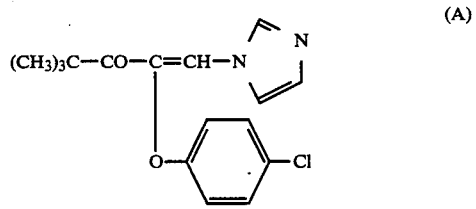

(A)

(B)

EXAMPLE A

Venturia test (apple)/protective
Solvent: 4 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation examples: 1 and 3.

EXAMPLE B

*Cochliobolus sativus* test (barley)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to the following preparation examples: 2 and 3.

EXAMPLE C

*Leptosphaeria nodorum* test (wheat)/protective
Solvent: 100 parts by weight of dimethylformamide
Emulsifier: 0.25 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Leptosphaeria nodorum*. The plants remain for 48 hours in an incubation cabinet at 20° C. and 100% relative atmospheric humidity.

The plants are placed in a greenhouse at a temperature of about 15° C. and a relative atmospheric humidity of about 80%.

Evaluation is effected 10 days after the inoculation.

In this test, a clearly superior activity compared with the prior art is shown, for example, by the compound according to the following preparation example: 1.

It will be understood that the specification and examples are illustrative but not limitative of the present invention and that other embodiments within the spirit and scope of the invention will suggest themselves to those skilled in the art.

We claim:

1. A cyclic azolylvinyl ether of the formula

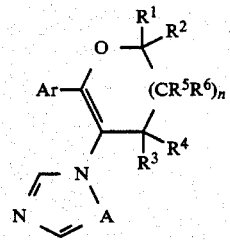

in which
A is a nitrogen atom or the CH group,
Ar is phenyl which is optionally substituted by halogen, alkyl or alkoxy with in each case 1 to 4 carbon atoms, halogenoalkyl, halogenoalkoxy or halogenoalkylthio with in each case 1 or 2 carbon atoms and 1 to 5 halogen atoms, nitro, cyano, in each case optionally halogen-substituted phenyl or phenoxy, and/or cycloalkyl with 5 or 6 carbon atoms,
$R^1$ to $R^6$ each independently is hydrogen or alkyl with 1 to 4 carbon atoms, and
n is 0 or 1, or an addition product thereof with an acid or metal salt.

2. A cyclic azolylvinyl ether or addition product according to claim 1,
in which
Ar is phenyl which is optionally mono-, di- or trisubstituted by fluorine, chlorine, bromine, methyl, ethyl, methoxy, trifluoromethyl, trifluoromethoxy, tri-fluoromethylthio, nitro, cyano, phenyl or phenoxy in each case optionally substituted by fluorine or chlorine, and/or cyclohexyl, and
$R^1$ to $R^6$ each independently is hydrogen, methyl, ethyl or isopropyl.

3. An ether according to claim 1, wherein such ether is 1-(4-biphenyl-yl)-2-(1,2,4-triazol-1-yl)-4,5-dihydropyran of the formula

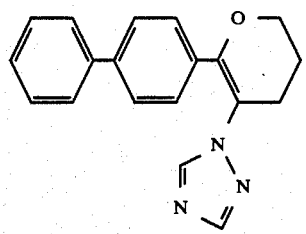

or an addition product thereof with an acid or metal salt.

4. An ether according to claim 1, wherein such ether is 1-(4-chlorophenyl)-2-(1,2,4-triazol-1-yl)-4,5-dihydropyran of the formula

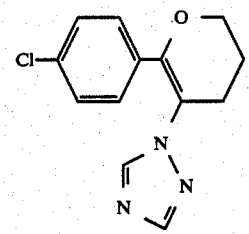

or an addition product thereof with an acid or metal salt.

5. An ether according to claim 1, wherein such ether is 1-(4-biphenyl-yl)-2-(imidazol-1-yl)-4,5-dihydropyran of the formula

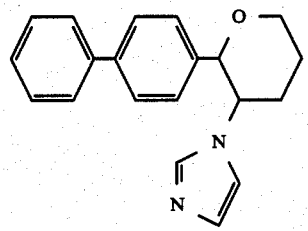

or an addition product thereof with an acid or metal salt.

6. A fungicidal composition comprising a fungicidally effective amount of an ether or addition product thereof according to claim 1 in admixture with a diluent.

7. A method of combating fungi which comprises administering to such fungi or to a fungus habitat a fungicidally effective amount of an ether or addition product thereof according to claim 1.

8. The method according to claim 7, wherein which ether is
1-(4-biphenyl-yl)-2-(1,2,4-triazol-1-yl)-4,5-dihydropyran,
1-(4-chlorophenyl)-2-(1,2,4-triazol-1-yl)-4,5-dihydropyran or
1-(4-biphenyl-yl)-2-(imidazol-1-yl)-4,5-dihydropyran, or an addition product thereof with an acid or metal salt.

* * * * *